(12) United States Patent
Pfefferle

(10) Patent No.: US 7,550,644 B2
(45) Date of Patent: Jun. 23, 2009

(54) ISOBUTANE ALKYLATION

(75) Inventor: William C. Pfefferle, Madison, CT (US)

(73) Assignee: Precision Combustion, Inc., North Haven, CT (US)

( * ) Notice: Subject to any disclaimer, the term of this patent is extended or adjusted under 35 U.S.C. 154(b) by 347 days.

(21) Appl. No.: 11/126,859

(22) Filed: May 10, 2005

(65) Prior Publication Data

US 2005/0250972 A1   Nov. 10, 2005

Related U.S. Application Data

(63) Continuation-in-part of application No. 11/115,512, filed on Apr. 27, 2005.

(60) Provisional application No. 60/569,599, filed on May 10, 2004.

(51) Int. Cl.
   C07C 2/54     (2006.01)
   C07C 2/58     (2006.01)

(52) U.S. Cl. .................... 585/720; 585/722; 585/714; 585/716

(58) Field of Classification Search ............... 585/714, 585/716, 720, 722
   See application file for complete search history.

(56) References Cited

U.S. PATENT DOCUMENTS

| | | | | |
|---|---|---|---|---|
| 2,002,394 | A * | 5/1935 | Frey | 585/714 |
| 3,541,180 | A * | 11/1970 | Thomas | 585/722 |
| 6,858,770 | B2 * | 2/2005 | Smith, Jr. et al. | 585/720 |
| 2005/0245782 | A1 | 11/2005 | Pfefferle | |

* cited by examiner

*Primary Examiner*—Thuan Dinh Dang
(74) *Attorney, Agent, or Firm*—Robert L. Rispoli

(57) ABSTRACT

A method for isobutane alkylation is provided using a fixed-bed catalytic alkylation reactor comprises at least one catalytic flow channel. A feed stream comprising a compound to be alkylated is passed into a flow channel having an alkylation catalyst positioned on at least a portion of the flow channel inner surface in the flow channel downstream region. Olefin is injected into the feed stream at a point beyond a flow channel entrance region whereby the olefin contacts the alkylation catalyst by diffusion to the flow channel inner surface thereby reacting the compound with the olefin and produces an alkylate product.

5 Claims, 3 Drawing Sheets

ISOBUTANE ALKYLATION

CROSS-REFERENCE TO RELATED APPLICATION

This application claims the benefit of U.S. Provisional Application No. 60/569,599 filed May 10, 2004. This application also is a continuation-in-part of U.S. patent application Ser. No. 11/115,512; filed Apr. 27, 2005, and incorporated herein by reference.

BACKGROUND OF THE INVENTION

1. Field of the Invention

The present invention relates to a method for catalytic isobutane alkylation. More particularly, the present invention is directed to a catalytic isobutane alkylation process that is advantageous for the alkylation of isobutane or benzene, as well as other compounds.

2. Description of the Related Art

Isobutane alkylation by reaction with an olefin is an important refinery process producing a high-octane alkane hydrocarbon product used to produce high-octane gasoline of low aromatic content. Commercial alkylation processes rely on use of either hydrogen fluoride or sulfuric acid catalyst systems. Unfortunately, both systems pose both environmental and safety hazards.

Hydrogen fluoride is an extremely toxic gas and thus even very small leaks are both a potentially lethal hazard for plant personnel and an area-wide health hazard. On the other hand, sulfuric acid is a burn hazard and the organics-contaminated spent acid is a toxic material that, if burned, creates sulfur oxide fumes. Consequently, it is an object of the present invention to provide a more environmentally benign alkylation process that could be used for alkylation of butane and aromatic compounds such as benzene. It is another object of the present invention to provide solid catalyst systems for use in heterogeneous fixed bed reactors.

With the development of synthetic zeolites, solid catalysts with a high activity for isobutane alkylation have become available. As is known in the art, zeolitic catalysts active for commercial alkylation processes also are active for olefin polymerization, a reaction that reduces alkylate octane and can produce high molecular weight polymers. Further, because the olefin polymerization reaction tends to be favored over the desired alkylation reaction, a very high ratio of isobutane-to-olefin must be used to reduce the probability of olefin-to-olefin polymerization.

In commercial alkylation processes, polymer formation produces sludge; however, it is merely a nuisance. In contrast, in an alkylation process employing a solid catalyst, polymer formation can block the active sites thereby requiring catalyst regeneration. Moreover, with both conventional and zeolite catalysts, the required high isobutane-to-olefin ratio increases operating cost because the unreacted isobutane must be recovered from the product stream and recycled. Unfortunately, polymer formation on a fixed-bed zeolitic catalyst results in catalyst deactivation in an economically unacceptable short time if operated at the isobutane-to-olefin ratio used in the commercial processes.

Accordingly, it is an object of the present invention to provide a catalytic isobutane alkylation process that overcomes these and other drawbacks associated with known commercial alkylation processes. It is yet another object of the present invention to provide a catalytic isobutane alkylation process that is advantageous regardless of the compound to be alkylated, most typically isobutane or benzene. The catalytic isobutane alkylation process according to the present invention is described with reference to isobutane.

BRIEF SUMMARY OF THE INVENTION

It has now been found that polymer formation on a fixed-bed alkylation catalyst can be reduced to an acceptable level in order to allow the use of known solid alkylation catalysts at isobutane-to-olefin ratios no higher than the ratios used in commercial isobutane alkylation processes. The present invention allows operation even at isobutane-to-olefin ratios lower than those required in current commercial processes. It has now been found that high isobutane ratios on the catalyst surface do not require high isobutane ratios for the feed streams. Although described in terms of isobutane alkylation, the method of the present invention is generic and applies to alkylation of any compound with an olefin.

The present invention promotes an economically feasible use of fixed bed catalysts. In addition, the present invention offers the potential to reduce the extent of isobutane required to be recycled to a value lower than that of present commercial processes. In accordance with the present invention, a fixed bed alkylation reactor can be operated in a mass-transfer controlled regime for the desired alkylation reaction with the olefin as the limiting reactant, such that the concentration of olefin on the surface will be minimal. The rate of diffusion of olefin to the catalyst surface is maintained sufficiently low such that olefin molecules react with isobutane before encountering another olefin molecule. Thus, the probability of olefin-olefin reaction (polymerization) is greatly reduced by limiting the rate of mass transfer of olefin to the catalyst surface to a value lower than that required for significant polymerization. In other words, the alkylation reaction must be mass transfer limited.

Excess olefin arriving at a catalyst surface tends to polymerize. As is known in the art, mass transfer rate to a solid surface is limited by boundary layer thickness. Thus, the rate of mass transfer to a catalytic surface in a flow channel can be controllably limited by choosing flow conditions which increase boundary layer thickness. Accordingly, laminar flow is preferred. Catalyst substrates that maximize mass transfer, such as for example pellet bed and ultra short channel length monolithic catalysts, are disadvantageous with presently known alkylation catalysts.

Catalyst substrates suitable for the present invention include conventional monolith catalysts having flow channel lengths more than long enough for full boundary layer build-up are preferred in the present invention. However, even monolith flow channels can have an entry region where the boundary layer is minimal and the mass transfer rate much too high. Thus, in the present invention it is preferred that the olefin be introduced only downstream of the monolith channel entrances. Further, because olefin polymerization tends to block catalyst sites, it is desirable that the mass transfer of olefin to the catalyst surface be sufficiently limited such that the olefin concentration on the surface is too low for significant polymerization even at the initial contact zone.

To achieve this, it has now been found that the olefin should be added to the process flow stream away from the flow channel walls at a point beyond the flow channel entrances. Advantageously, the flow velocity of the olefin flow should match that of the surrounding channel flow. As is well known in the art, diffusion rate to a surface is determined by distance and concentration gradient. Thus, the flow channel diameter and the olefin concentration in the olefin feed stream can be chosen such that the rate of delivery of olefin to the catalyst surface is always mass transfer limited to a value low enough to minimize polymerization to a desired level. Advantageously, olefin is injected into the flow stream at multiple points along flow channel centerlines to maximize the conversion of isobutane to alkylate. This allows a higher conversion of isobutane per pass yet minimizes olefin polymerization. Benzene and other compounds may be alkylated in the method of the present invention.

DETAILED DESCRIPTION OF THE INVENTION

Figure 1:
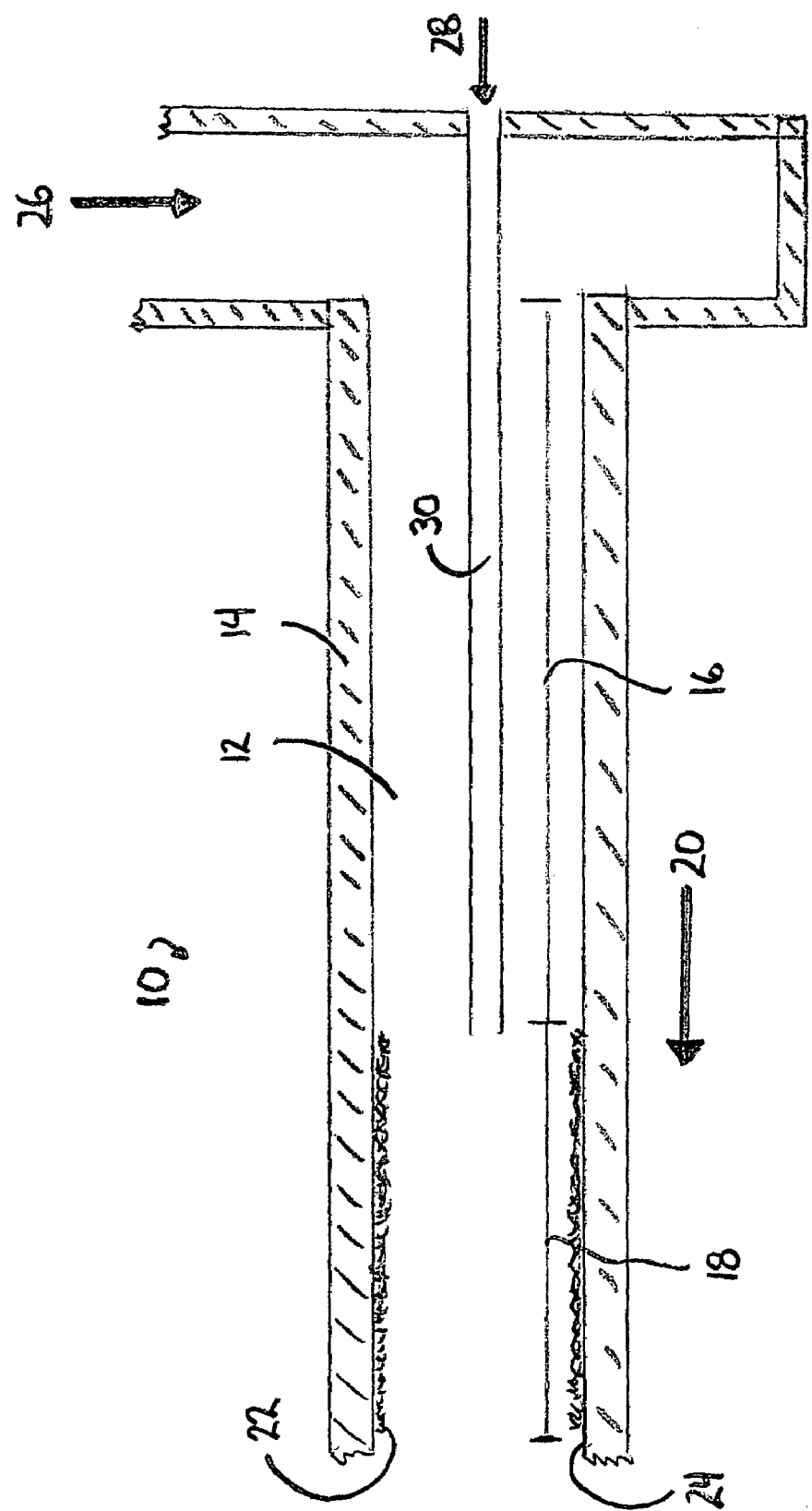
FIG. 1, FIG. 2 and FIG. 3 depict diagrammatic section representations of reactors according to the present invention.

As depicted in FIG. 1, the catalytic isobutane alkylation reactor 10 comprises an alkylation reactor flow channel 12 that defines flow channel wall 14. Flow channel 12 further defines entrance region 16 and downstream region 18, wherein downstream flow 20 indicates the direction of flow through the reactor. An alkylation catalyst 22 is positioned on the inner face 24 of channel wall 14 in downstream region 18. The upstream position limit of catalyst 22 defines a transition point between entrance region 16 and downstream region 18. Catalyst 22 may be positioned on only a portion of inner face 24 of channel wall 14 in downstream region 18.

Isobutane 26 is introduced into the reactor 10 passing therethrough into entrance region 26. The isobutane flow rate is such that flow is laminar in downstream region 18. Olefin 28 is introduced into the reactor 10 through injection tube 30 and exits tube 30 along the centerline of flow channel 12. No catalyst is needed on inner face 24 in entrance region 16, but may be present.

Figure 2:
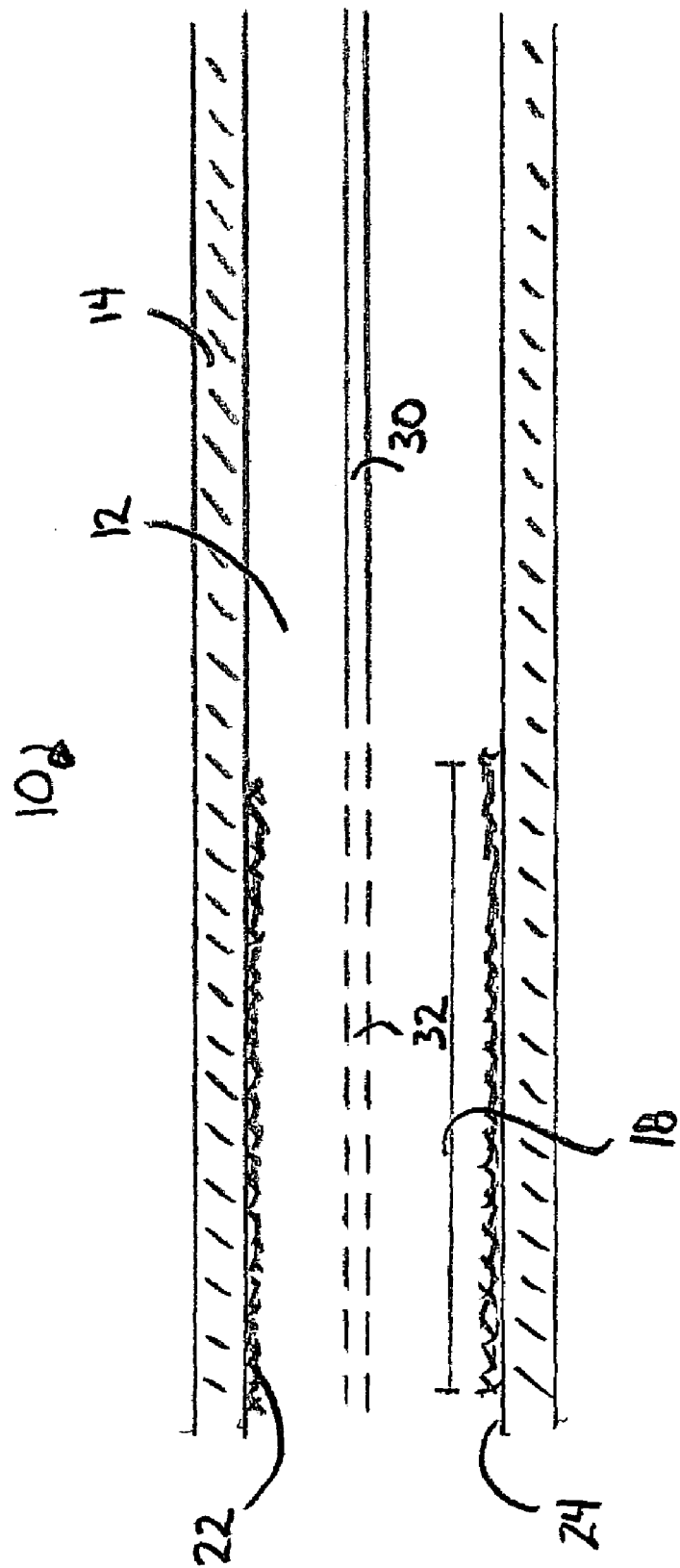

FIG. 2 depicts another embodiment of catalytic isobutane alkylation reactor 10 wherein injection tube 30 delivers olefin to porous tube 32 which provides olefin to the surrounding isobutane flow thereby maintaining a nominally constant olefin flow to the catalyst 22 positioned on the inner face 24 of channel wall 14 in downstream region 18.

Figure 3:
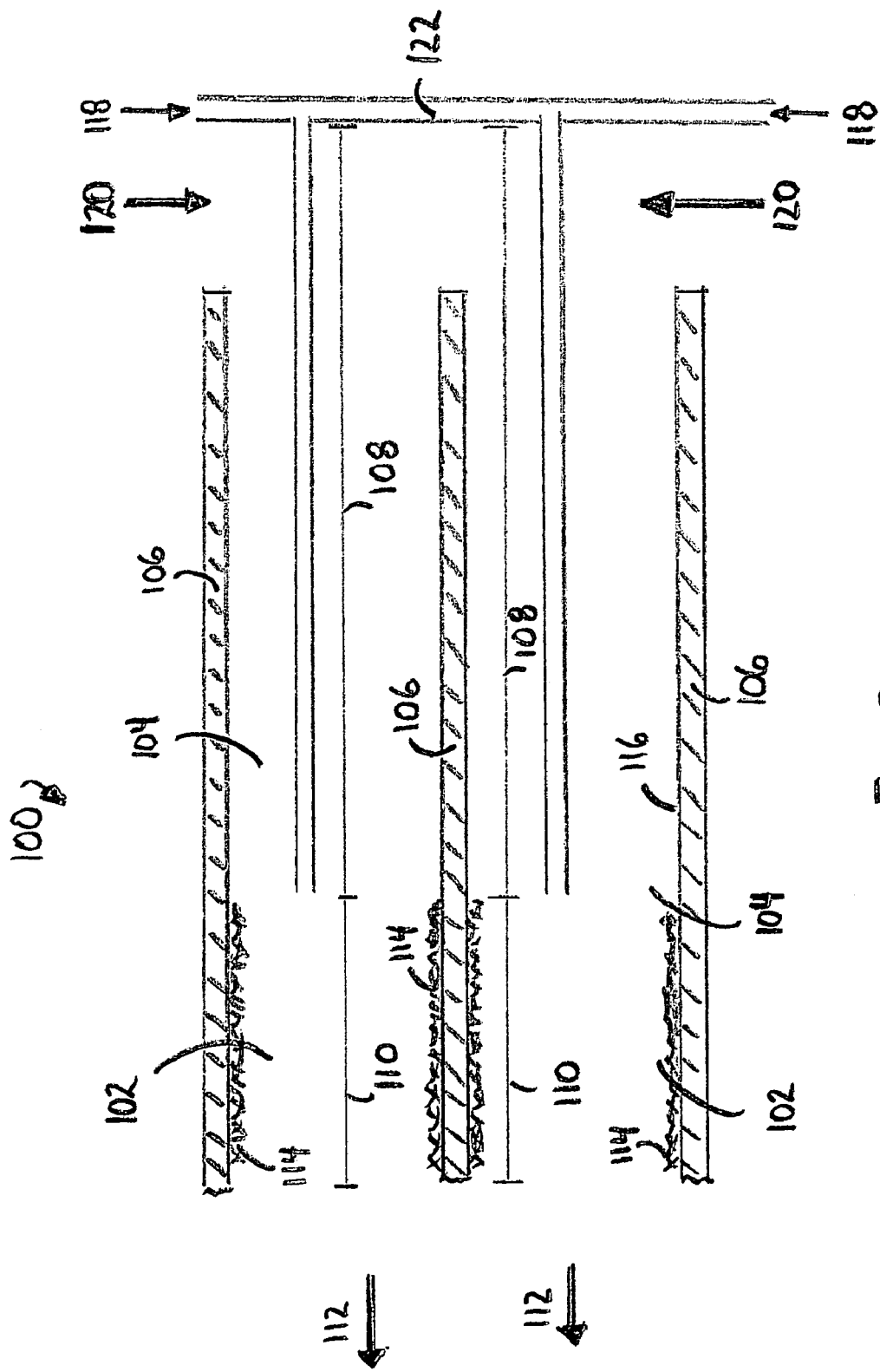

FIG. 3 depicts yet another embodiment of the present invention. Catalytic isobutane alkylation reactor 100 comprises two flow channels of monolith 102. Each monolith 102 comprises an alkylation reactor flow channel 104 that defines flow channel wall 106. Flow channel 102 further defines entrance region 108 and downstream region 110, wherein downstream flow 112 indicates the direction of flow through the reactor. An alkylation catalyst 114 is positioned on the inner face 116 of channel wall 106 in downstream region 110. The upstream position limit of catalyst 114 defines a transition point between entrance region 108 and downstream region 110. Catalyst 114 may be positioned on only a portion of inner face 1 16 of channel wall 106 in downstream region 110.

Isobutane 120 is introduced into the reactor 100 passing therethrough into entrance region 108. The isobutane flow rate is such that flow is laminar in downstream region 110. Olefin 118 is introduced into the reactor 100 through injection tube 122 and exits tube 122 along the centerlines of flow channels 104. No catalyst is needed on inner face 116 in entrance region 108, but may be present Although the invention has been described in considerable detail, it will be apparent that the invention is capable of numerous modifications and variations, apparent to those skilled in the art, without departing from the spirit and scope of the invention. For example, although conventional monolith structures make possible compact reactors, reactors comprising individual tubes may be used and make possible longer reactors thereby taking full advantage of the method of the present invention.

What is claimed is:

1. A method of operating a fixed-bed alkylation reactor with reduced polymerization of olefin comprising:
   a) obtaining a feed stream containing isobutane;
   b) passing the feed stream into a flow channel wherein the flow channel defines a flow channel entrance region having no active alkylation catalyst positioned thereon, and a flow channel downstream region, the flow channel downstream region further defining a flow channel inner surface with an alkylation catalyst positioned on at least a portion of the flow channel inner surface thereby defining a transition point between the flow channel entrance region and the flow channel downstream region;
   c) injecting an olefin into said feed stream at a point beyond the transition point into the flow channel downstream region, whereby the olefin contacts the alkylation catalyst by diffusion to the flow channel inner surface thereby reacting isobutane with the olefin; and
   d) producing an alkylate product, wherein the reactor comprises a structural configuration monolith.

2. The method of claim 1 wherein the monolith further comprises a plurality of flow channels, each flow channel defining a flow channel entrance region, a flow channel downstream region and a flow channel inner surface, and an alkylation catalyst positioned on at least a portion of the flow channel inner surface of at least one flow channel downstream region.

3. The method of claim 2 wherein the alkylation catalyst comprises a zeolite.

4. The method of claim 1 wherein the olefin is introduced at multiple points along a centerline of the flow channel.

5. The method of claim 2 wherein the olefin is introduced into a plurality of the flow channels at multiple points along centerlines of the flow channel downstream regions.

* * * * *